United States Patent [19]

Magarian et al.

[11] Patent Number: 5,324,736
[45] Date of Patent: Jun. 28, 1994

[54] DIPHENYLCYCLOPROPYL ANALOGS AS ANTIESTROGENIC AND ANTITUMOR AGENTS

[75] Inventors: Robert A. Magarian; Joseph T. Pento, both of Norman, Okla.; Kwasi S. Avor, Columbia, Mo.

[73] Assignee: Research Corporation Technologies, Inc., Tucson, Ariz.

[21] Appl. No.: 107,426

[22] Filed: Aug. 16, 1993

Related U.S. Application Data

[63] Continuation of Ser. No. 812,246, Dec. 19, 1991, which is a continuation-in-part of Ser. No. 432,564, Nov. 6, 1989, Pat. No. 5,098,903, which is a continuation-in-part of Ser. No. 98,945, Sep. 21, 1987, Pat. No. 4,879,315, which is a continuation-in-part of Ser. No. 363,429, Mar. 30, 1982, abandoned, which is a continuation-in-part of Ser. No. 166,255, Jul. 7, 1980, abandoned, which is a continuation-in-part of Ser. No. 128,040, Mar. 7, 1980, abandoned.

[51] Int. Cl.$^5$ ............... A61K 31/445; A61K 31/495; C07D 211/20
[52] U.S. Cl. ................... 514/317; 514/252; 546/236; 544/336
[58] Field of Search ............... 546/236; 514/317

[56] References Cited

PUBLICATIONS

Hausser et al., "Solvolysis of Cyclopropyl Halides. III. 2,3-Diphenylcyclopropyl Chlorides", J. Org. Chem., 37:4087-4090 (1972).

Magarian et al., "2-Chloro-1-phenylindene from 1,1-Dichloro-trans-2,3-diphenylcyclopropane", J. Pharmaceutical Sciences, 61:1216-1219 (1972).

Magarian et al., "Synthesis of Cyclopropyl Analogs of Stilbene and Stilbenediol as Possible Antiestrogens", J. Phar. Sci. 64:1626-1632 (1975).

Primary Examiner—Cecilia Tsang
Attorney, Agent, or Firm—Dunlap Codding Lee

[57] ABSTRACT

Diphenylcyclopropyl analogs in which one or more of the phenyl rings includes substituents comprising a hydroxy group, a hydrogen atom, an acetate group or a substituted or unsubstituted alkoxy group. The compounds are useful as antiestrogens and anti-tumor agents.

44 Claims, No Drawings

DIPHENYLCYCLOPROPYL ANALOGS AS ANTIESTROGENIC AND ANTITUMOR AGENTS

GOVERNMENTAL SUPPORT FOR INVENTION

This invention was made with Government support under a grant from the National Cancer Institute (CA40458). The Government has certain rights in this invention.

CROSS-REFERENCE TO RELATED APPLICATIONS

This application is a Continuation of U.S. patent application Ser. No. 07/812,246 filed on Dec. 19, 1991 which is a continuation-in-part of U.S. patent application Ser. No. 07/432,564, filed Nov. 6, 1989, U.S. Pat. No. 5,098,903, which is a continuation-in-part of U.S. patent application No. 07/098,945, filed Sep. 21, 1987 (U.S. Pat. No. 4,879,315), which is a continuation-in-part of U.S. patent application Ser. No. 06/363,429, filed Mar. 30, 1982 (ABAN), which is a continuation-in-part of U.S. patent application Ser. No. 06/166,255, filed Jul. 7, 1980 (ABAN), which is a continuation-in-part of U.S. patent application Ser. No. 06/128,040 filed Mar.7, 1980 (ABAN). U.S. patent application Ser. No. 06/410,938, filed Sep. 22, 1989 (U.S. Pat. No. 5,015,666), entitled Triarylcyclopropanes as Antiestrogens and Antitumor Agents discloses related subject matter.

These applications are incorporated herein by reference.

FIELD OF THE INVENTION

This invention relates to diphenylcyclopropyl analog compounds and their use in mammals for producing anti-estrogenic activity in the mammal, and for inhibiting the development of an estrogen-dependent tumor in the mammal.

SUMMARY OF THE INVENTION

The present invention comprises a compound having the formula:

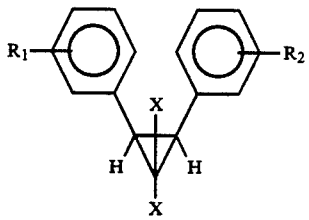

or any pharmaceutically acceptable salt thereof. X is a halogen or hydrogen. $R_1$ is a hydrogen atom, an acetate group, or a hydroxyl group. R1 may also be an alkoxy group or a substituted alkoxy group in which the substituent of the alkoxy group comprises either dialkylamino group in which the alkyl substituent contains 1 to 6 carbons, an alkylsulfonyloxy group in which the alkyl substituent contains 1 to 6 carbons, or a substituted or unsubstituted heterocycle containing about 5 to 7 members. At least one of the members of the heterocycle group is nitrogen. The heterocycle substituent is an alkyl group containing from 1 to about 6 carbon atoms. The composition may also comprise pharmaceutically acceptable salts of the foregoing.

$R_2$ is a hydrogen atom, an acetate group, or a hydroxyl group. R1 may also be an alkoxy group or a substituted alkoxy group in which the substituent of the alkoxy group comprises either dialkylamino group in which the alkyl substituent contains 1 to 6 carbons, an alkylsulfonyloxy group in which the alkyl substituent contains 1 to 6 carbons, or a substituted or unsubstituted heterocycle containing about 5 to 7 members. At least one of the members of the heterocycle group is nitrogen. The heterocycle substituent is an alkyl group containing from 1 to about 6 carbon atoms. The composition may also comprise pharmaceutically acceptable salts of the foregoing.

In the compound of the Present invention, R1 and R2 are as described above provided that both R1 and R2 cannot be hydrogen, hydroxy, acetate or methoxy.

The compounds of the present invention may be combined with a pharmaceutically acceptable carrier to form pharmaceutical compositions.

The present invention further comprises a method of inducing antiestrogenic activity in a mammal in need of such therapy comprising administering to the mammal an anti-estrogenically effective amount of one or more compounds having the above-described formula.

The present invention also comprises a method of inhibiting the development of an estrogen-dependent tumor in a mammal in need of such therapy comprising administering to the mammal an effective amount of one or more compounds having the above-described formula.

DETAILED DESCRIPTION OF THE PREFERRED EMBODIMENTS

The present invention comprises a compound having the formula:

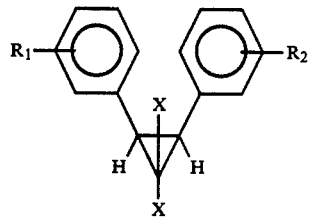

or any pharmaceutically acceptable salt thereof.

X represents a halogen or a hydrogen. Preferably X is chlorine.

$R_1$ represents a hydrogen atom, an acetate group, or a hydroxyl group. R1 may also represent an alkoxy group containing from 1 to 3 carbon atoms, and more preferably, from 2 to 3 carbon atoms. $R_1$ may also be a substituted alkoxy group in which the alkyl portion thereof contains 1-3 carbon atoms and preferably between 2-3 carbons, and in which the alkyl portion thereof is substituted with one of the following groups: a dialkylamino group, an alkylsulfonyloxy group, or a substituted or unsubstituted heterocycle containing about 5 to 7 members, one of which is nitrogen. Preferably the heterocycle group contains 5 or 6 members and most perferably contains 6 members.

If $R_1$ is a substituted alkoxy group, and if the alkoxy group substituent is a dialkylamino group, the alkyl portion of the dialkylamino substituent group on the $R_1$ alkoxy group preferably contains 1 to 6 carbons, and more preferably 2 to 3 carbons, and most preferably is a beta-dialkylethoxy group. Examples of preferred dialkylaminoalkoxy groups include dimethylaminoethoxy and diethylaminoethoxy groups.

If $R_1$ is a substituted alkoxy group, and if the alkoxy group substituent is an alkylsulfonyloxy group, the alkyl portion of the alkylsulfonyloxy substituent group on the R1 alkoxy group preferably contains 1 to 6 carbons, and more preferably 1 to 3 carbons. An example of a preferred alkylsulfonyloxy alkoxy group is methanesulfonyloxyethoxy.

If $R_1$ is a substituted alkoxy group, and if the alkoxy group substituent is a substituted or unsubstituted heterocycle containing 5 to 7 members, the heterocycle substituent preferably contains at least one nitrogen and more preferably 1 to 2 nitrogens. Preferred heterocycles include piperidino and piperazino groups. Other saturated and unsaturated heterocycles containing nitrogen may also be used, including heterocycles containing oxygen.

If the heterocycle substituent group on the $R_1$ alkoxy group is substituted, it preferably is substituted with an alkyl group. The substituent alkyl group preferably contains from 1 to about 6 carbon atoms, and more preferably contains from 1 to 3 carbon atoms. A preferred example of an alkyl substituted heterocycle alkoxy group is a methylpiperazinoethoxy group.

In the compounds of the present invention any of the foregoing groups described herein as being represented by $R_1$ may also be at the $R_2$ position provided that both $R_1$ and $R_2$ may not both be simultaneously hydrogen, simultaneously hydroxy, simultaneously methoxy or simultaneously acetate. The $R_1$ and $R_2$ groups may be at any position on the respective phenyl group; however, the para positions are preferred.

When the compound of the present invention is optically active, each optical isomer thereof, as well as racemic mixtures One particularly preferred compound of the present invention comprises (Z)-1,1-Dichloro-2-[4-(2-methanesulfonyloxyethoxy)phenyl]3-phenylcyclopropane:

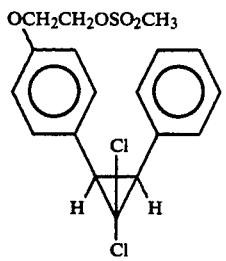

including each of its (R) and (S) optical isomers and racemic mixtures thereof.

Another preferred compound is (Z)-1,1-Dichloro-2-[4-[2-(dimethylamino)ethoxy]-phenyl]-3-phenylcyclopropane:

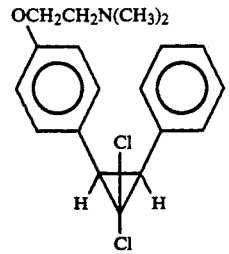

each of its (R) and (S) optical isomers and racemic mixtures thereof.

Another preferred compound is (Z)-1,1-Dichloro-2-[4-[2-(diethylamino)ethoxy]-phenyl]-3-phenylcyclopropane:

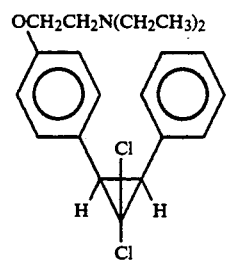

including each of its (R) and (S) optical isomers and racemic mixtures thereof.

Another preferred compound is (Z)-1,1-Dichloro-2-[4-[2(piperidino)ethoxy]-phenyl]-3-phenylcyclopropane:

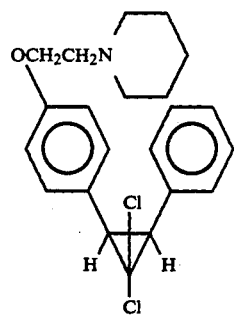

including each of its (R) and (S) optical isomers and racemic mixtures thereof.

Yet another preferred compound is (Z)-1,1-Dichloro-2-[4-[2-(N-methylpiperazino)ethoxy]-phenyl]-3-phenylcyclopropane:

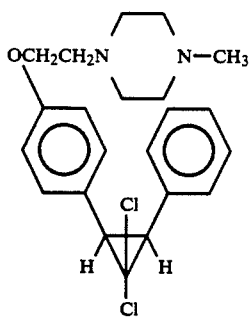

including each of its (R) and (S) optical isomers and racemic mixtures thereof.

Preferably, the compounds of the present invention are combined with a pharmaceutically acceptable carrier to form a pharmaceutical composition appropriate for therapeutic delivery to a mammal. The pharmaceutically acceptable carrier should not substantially interfere with the anti-estrogenic and anti-tumor activities of the compound, and may be a solid or liquid in which the compound is solubilized, suspended or dispersed in any manner.

The compounds of the present invention may be administered orally in solid dosage forms, such as tablets and powders, or in liquid dosage forms, such as elixirs, syrups and suspensions; they may also be administered parenterally, in sterile liquid dosage forms. Such parenteral administration may include intravenous, intramuscular, subcutaneous, intra-arterial, and direct tumor perfusion techniques.

If the compound is to be injected, the pharmaceutical carrier should preferably be isotonic, and have about a physiological pH. Suitable pharmaceutical carriers for parenteral administration may be any suitable oil, saline, aqueous dextrose or related sugar solutions, or glycols such as propylene glycol or polyethylene glycols. Solutions for parenteral administration contain preferably a water soluble salt of the active ingredient, suitable stabilizing agents, and if necessary, buffer substances. Additionally, parenteral solutions can contain preservatives. Other suitable pharmaceutical carriers are described in *Remington's Pharmaceutical Sciences*, Mack Publishing Co., and similar reference texts.

The present invention further comprises a method of inducing antiestrogenic activity in a mammal, such as a human, in need of such therapy comprising administering to the mammal an antiestrogenically effective amount of one or more compounds having the formula, preferably in the form described above. The dosage of the compounds of the present invention may vary due to the therapeutically desired result which is affected by the type of disease or condition in the mammal; the age, weight and health of the recipient; the severity of the condition or disease in the mammal; the kind of concurrent treatment, if any, being administered to the mammal; and the frequency of treatment. Generally, a therapeutically effective dosage is less than about 0.5 mg to about 2 mg per kilogram of body weight of the mammal over a 24 hour period. The method of administration of the compound of the present invention can be by any suitable method as previously described.

The present invention also comprises a method of inhibiting the development of an estrogen-dependent tumor in a mammal, such as a human, in need of such therapy comprising administering to the mammal a therapeutically effective amount of one or more compounds having the formula described above, preferably in the form of a pharmaceutical composition comprising at least one of the compounds combined with a pharmaceutically acceptable carrier. "Inhibiting the development of an estrogen-dependent tumor" means either slowing the growth of a tumor, diminishing the size of a tumor, or preventing the formation of a tumor from cells having the potential of developing into a tumor wherein the tumor requires the presence of an estrogenic substance for the growth, development and/or metastatic involvement of the tumor.

The compounds previously described may be administered to the mammal to inhibit the development of the estrogen-dependent tumor by an administration method of the type previously described. The dosage may vary according to the type of the disease; the size of the tumor or tumors, if present; and the quantity of tumors as well as other factors previously described. Generally, a daily dosage of less than about 0.5 mg to about 2 mg/kg of body weight of the mammal will suffice.

The following examples illustrate the practice of the present invention.

EXAMPLE 1

Preparation of (Z)-1,1-Dichloro-2-[4-(2-methane-sulfonyloxyethoxy)-phenyl]-3-phenylcyclopropane (Compound 7)

A mixture of p-hydroxybenzaldehyde (40.30g, 0.33mol), 2-chloroethyl methyl ether (31.20g 0.33mol) and $K_2CO_3$ (45.61g, 0.33mol) in DMF (100mL) was refluxed for 12h. The resulting orange mixture was diluted with water (100mL) and extracted three times with 50mL of $CHCl_3$. The organic layers were combined and washed with 5% NaOH, brine and dried over anhydrous $MgSO_4$. It was filtered and evaporated in vacuo to give brown liquid which was distilled on the Kuqelrohr distillation apparatus to obtain yellowish liquid (51.40g, 87%) at room temperature but solid in the cold. NMR ($CDCl_3$) δ 3.40 (s, 3H, $OCH_3$), 3.60–3.90 (m, 2H, $OCH_2$), 4.10–4.40 (m, 2H, $OCH_2$), 7.00–7.80 (dd, 4H, substituted ArH), 9.90 (s, 1H, CHO). This procedure produces 4-[2-(methoxy)ethoxy]benzaldehyde.

To phenylacetic acid (66.12g, 0.49mol) was added acetic anhydride (75mL), the acid dissolved with continuous stirring to give a light yellow solution. Triethylamine (45mL) was added, 4-[2-(methoxy)ethoxy]benzaldehyde (58.34g, 0.32mol) was added slowly through a dropping funnel and the mixture refluxed for 36h. The mixture was allowed to cool to room temperature and transferred to a separatory funnel with 100mL of $Et_2O$. Four 40mL portions of 30% NaOH solution was used to extract the $Et_2O$ mixture. The combined basic layers were washed with two 50mL portions of $Et_2O$ which were discarded. The basic solution was then acidified with concentrated HCl to give a solid precipitate which was recrystallized from 95% ethanol to give light yellow needles (48.86g, 52%), m.p. 154°–156° C. NMR ($CDCl_3$) δ 3.40 (s, 3H $OCH_3$), 3.60–3.90 (m, 2H, $OCH_2$), 4.00–4.20 (m, 2H, $OCH_2$), 6.70 and 7.05 (dd, 4H, substituted ArH), 7.20–7.50 (m, 5H, ArH), 7.95 (s, 1H, C═CH). This procedure produces (Z)-α-Phenyl-β-[4-(2-methoxy)ethoxy] cinnamic acid.

A 500mL, three necked, round bottom flask equipped with a condenser, with a gas trap, a thermometer and a magnetic stirrer was utilized. To a solution of (Z)-α-Phenyl β- [4-(2-methoxy) ethoxy]cinnamic acid (20.00g, 0.07mol) in quinoline (90.41g, 0.70mol) was added copper chromite (1.46g, 0.005mol) and heated. Carbon dioxide evolved when the temperature reached 190° C. The mixture was kept within 200°–210° C. for 3h, cooled to room temperature and filtered under vacuum. The black mixture was transferred to a separatory funnel with 100mL of $Et_2O$ and extracte with five 50mL portions of 20% HCl solution to remove the residual quinoline. The $Et_2O$ layers were washed with brine, dried over $MgSO_4$ and concentrated in vacuo. The resulting brown oil was purified by flash chromatography (silica gel, 50/50 $CH_2Cl_2$/ petroleum ether) to obtain cis stilbene 4 (15.61g, 91%) as a very light yellow oil. NMR (CDCl$_3$) δ 3.40 (s, 3H, OCH$_3$), 3.60–3.90 (m, 2H, OCH$_2$), 4.00–4.20 (m, 2H, OCH$_2$), 6.55 (s, 2H, C=CH), 6.80 and 7.20 (dd, 4H, substituted ArH), 7.30 (s, 5H, ArH). This procedure produces (Z)-1-[4-(2-methoxyethoxy)phenyl]-2-phenylethylene.

To (Z)-1-[4-(2-methoxyethoxy)phenyl]-2-phenylethylene (15.61g, 0.06mol) dissolved in CHCl$_3$ (193mL) was added triethyl-benzyl-ammonium chloride (0.98g, 0.004mol), chilled 40% NaOH solution (96.00g, 2.40mol) was added slowly through a dropping funnel according to the method of Dehmlow and Schonefeld, *J. Liebigs Ann Chem.* 744:42(1971) and the mixture stirred for 80h. The resulting brown emulsion was poured onto 200mL water in a separatory funnel and the layers were separated, the aqueous layer was extracted with three 50mL portions of $CH_2Cl_2$, the combined organic extracts were washed with brine, dried over $MgSO_4$, filtered and evaporated in vacuo to obtain a dark brown oil which was purified by flash chromatography (50:50 $CH_2Cl_2$/petroleum ether) to give a colorless oil (19.70g, 80%). NMR (CDCl$_3$) δ 3.30 (s, 2H, ArCH), 3.50 (s, 3H, OCH$_3$), 3.65–3.85 (m, 2H, OCH$_2$), 4.00–4.25 (m, 2H, OCH$_2$), 6.85–7.40 (m, 9H, ArH). This procedure produces (Z)-1,1-Dichloro-2-[4-(2-methoxyethoxy)phenyl]-3-phenylcyclopropane.

To (Z)-1,1-Dichloro-2-[4-(2-methoxyethoxy)phenyl]-3phenylcyclopropane (14.10g, 0.04mol) in CH$_3$CN (100mL) was added sodium iodide (25.07g, 0.17g). The reaction flask was fitted with a gas trap, an argon inlet and a rubber septum. The reaction flask was then flushed with argon. By means of a syringe, chlorotrimethylsilane (21mL) was injected into the reaction flask through the rubber septum and the mixture stirred at room temperature for 24 hours. Water (100mL) was then added to the mixture and extracted with three 50mL portions of ethyl acetate. The organic extracts were combined and washed with sodium thiosulfate solution till the organic extract became colorless, then dried over anhydrous MgSO$_4$ and evaporated in vacuo to obtain an oil. The oil was purified by flash chromatography and eluted with CH$_2$Cl$_2$ to give a colorless oil (10.79g, 80%). NMR (CDCl$_3$) δ 2.20 (broad, 1H, OH), 3 30 (s, 2H, ArCH), 3.90–4.20 (m, 4H, OCH$_2$CH$_2$OH), 6.80–7.50 (m, 9H, ArH). This procedure produces (Z)-1,1-Dichloro-2-[4-(2-hydroxy-ethoxy)-pheny]-3-phenylcyclopropane.

Triethylamine (14.87g, 0.15 mol) was added to a solution (Z)-1,1-Dichloro-2-[4-(2-hydroxyethoxy)-pheny]-3-phenylcyclopropane (10.78g, 0.03mol) and methanesulfonyl chloride (16.81g, 0.15mol) in THF (50mL) at 0° C. After 1h water (50mL) was added to the reaction mixture and transferred to a separatory funnel. The mixture was extracted three times with 30mL portions of ethyl acetate, dried over MgSO$_4$ and concentrated in vacuo to give a light yellow oil. The oil was purified by flash chromatography (50:50 CH$_2$Cl$_2$/petroleum ether) to give a colorless oil (11.65g, 87%). NMR (CDCl$_3$) δ 3.10 (s, 3H, OSO$_2$CH$_3$), 3.30 (s, 2H, ArCH), 4.10–4.30 (m, 2H, OCH$_2$OSO$_2$CH$_3$), 4.50–4.70 (m, 2H, ArOCH$_2$), 6.80–7.40 (m, 9H, ArH).

EXAMPLE 2

Preparation of (Z)-1,1-Dichloro-2-[4-[2-(dimethylamino)ethoxy]-phenyl]-3-phenylcyclopropane (Compound 8)

To the (Z)-1,1-Dichloro-2-[4-(2-methanesulfonyloxyethoxy)phenyl]-3-phenylcyclopropane (1.00g, 0.003mol) in 25mL CH$_3$CN was added dimethylamine hydrochloride (2.45g, 0.03mol) and the mixture cooled in dry ice/acetone bath for 25min. Flame dried K$_2$CO$_3$ (8.29g, 0.06mol) was then added and the flask stoppered with a rubber septum so as to trap the gaseous dimethylamine. The slurry mixture was stirred at room temperature for 48h after which 25mL of water was added and extracted with three portions of 10mL Et$_2$O. The Et$_2$O extracts were combined, dried over MgSO$_4$ and evaporated in vacuo, the residue was purified by flash chromatography and eluted with EtOAc to give a light yellowish oil. The oil was dissolved in 25mL Et$_2$O and extracted with 10mL portions of 30% HCl solution until the Et$_2$O layer became clear. The combined aqueous extracts were treated with 20% NaOH solution to pH 11, and extracted with three portions of 20mL Et$_2$O. The combined Et$_2$O extracts were washed with water, dried over MgSO$_4$ and concentrated in vacuo to obtain a light yellow oil (0.60g, 71%). NMR (CDCl$_3$) δ 2.35 (s, 6H, N(CH$_3$)$_2$), 2.70 (t, 2H, CH$_2$N), 3.30 (s, 2H, ArCH), 4.05 (t, 2H, OCH$_2$), 6.90–7.40 (m, 9H, ArH).

Citrate Salt: The oil (Z)-1,1-Dichloro-2-[4-[2-(dimethylamino)ethoxy]-phenyl]-3-phenylcyclopropane was dissolved in hot EtOH and treated with an equal amount of citric acid in hot EtOH and treated with an equal molar amount of citric acid in hot EtOH. The citrate salt was recrystallized from EtOH and obtained as a white powder in 81% yield, mp: 67°–68° C.

EXAMPLE 3

Preparation of (Z)-1,1-Dichloro-2-[4-[2-(di-ethylamino)ethoxy]-phenyl]-3-phenylcyclopropane Compound 9)

Diethylamine (10mL) and Et$_3$N (10mL) were added to a solution of (Z)-1,1-Dichloro-2-[4-(2-methanesulfonyloxyethoxy)phenyl]-3-phenylcyclopropane (1.00g, 0.003mol) in acetonitrile (20mL). The orange solution was stirred at room temperature for 48h after which the volatile components were evaporated in vacuo and the residue purified by flash chromatography eluting with EtOAc to give an orange oil. Further purification was carried out by acid/base extraction as in the procedure for (Z)-1,1-Dichloro-2-[4-[2-(dimethylamino)ethoxy]-phenyl]-3-phenylcyclopropane to obtain a light orange oil (0.66g, 70%) NMR (CDCl$_3$) δ 1.15 (t, 6H, NCH$_2$CH$_3$), 2.50–3.00 (m, 6H, OCH$_2$CH$_2$ and NCH$_2$CH$_3$), 3.30 (s, 2H, ArCH), 4.10 (t, 2H, OCH$_2$), 6.90–7.40 (m, 9H, ArH).

Citrate Salt: The oil (Z)-1,1-Dichloro-2-[4-[2-(diethylamino)ethoxy]-phenyl]-3-phenylcyclopropane was dissolved in hot EtOH and treated with an equal amount of citric acid in hot EtOH. The citrate salt was recrystallized from EtOH and obtained as a white powder in 83% yield, mp: 101°-102° C.

EXAMPLE 4

Preparation of (Z)-1,1-Dichloro-2-[4-[2-(piperidino)ethoxy]-phenyl]-3-phenylcyclopropane (Compound 10)

This compound was prepared according to the procedure used to synthesize (Z)-1,1-Dichloro-2-[4-[2-(diethylamino)ethoxy]phenyl]-3-phenylcyclopropanc described herein using (Z)-1,1-Dichloro-2-[4-(2-methanesulfonyloxyethoxy)phenyl]-3-phenylcyclopropane (1.00g, 0.003mol) and piperidine (10mL). The compound was obtained as a light orange oil (0.84g, 87%). NMR (CDCl$_3$) δ 1.40–1.70 (m, 6H, ring CH$_2$ nonadjacent to N), 2.40–2.60 (broad m, 4H, CH$_2$ adjacent to N), 2.75 (t, 2H, CH$_2$N), 3.30 (s, 2H, ArH), 4.10 t, 2H,OCH$_2$), 6.80–7.40 (broad m, 9H, ArH).

Citrate Salt: The oil (Z)-1,1-(Dichloro-2-[4-[2-(piperidino)ethoxy]-phenyl]-3-phenylcyclopropane was dissolved in hot EtOH and treated with an equal amount of citric acid in hot EtOH. The citrate salt was recrystallized from EtOH and obtained as a white powder in 85% yield, mp: 96°-100° C.

EXAMPLE 5

Preparation of (Z)-1,1-Dichloro-2-[4-[2-(N-methylpiperazino)ethoxy]-phenyl]-3 phenylcyclopropane (Compound 11)

This compound was prepared according to the procedure used to synthesize (Z)-1,1-Dichloro-2-[4-(2-diethylamino)ethoxy]-phenyl]-3phenylcyclopropane described herein using (Z)-1,1-Dichloro-2-[4(2-methanesulfonyloxyethoxy)phenyl-3-phenylcyclopropane (1.00g, 0.003mol) and N-methyl piperazine (10mL). The product was obtained as a colorless oil (0.82g, 81%). NMR (CDCl$_3$) δ 2.27 (s, 3H, NCH$_3$), 2.39–2.70 (broad m, 8H, ring CH$_2$), 2.80 (t, 2H, CH$_2$N), 3.30 (s, 2H, ArCH), 4,05 (t, 2H, OCH$_2$), 6.90–7.4o (m, 9H, ArH).

Citrate Salt: The oil (Z)-1,1-Dichloro-2-[4-[2-(N-methylpiperazino)ethoxy]-phenyl]-3-phenylcyclopropane was dissolved in hot EtOH and treated with an equal amount of citric acid in hot EtOH. The citrate salt was recrystallized from EtOH and obtained as a white powder in 90% yield, mp: 101°-102° C.

EXAMPLE 6

Biological Testing

The biological evaluation of the test compounds consisted of the in vitro rat cytosolic estradiol receptor binding assay, the in vivo immature mouse uterotrophic (estrogenic) assay, and the in vivo immature mouse and rat antiuterotrophic (antiestrogenic) assay and in the in vitro suppression of the proliferation of the MCF-7 human breast cancer cell line. All assays contained estradiol, TAM, MER 25, and 1-1-dichloro-2 3-cis-diphenylcyclopropane (Analog II) as standards.

Biological Assays. Tamoxifen was obtained from Stuart Pharmaceutical, Division of ICI Americas, Inc., Wilmington, Delaware. MER 25 was obtained from Merrell Dow Research Institute, Division of Merrell Dow Pharmaceuticals, Inc., Cincinnati, Ohio. Absolute ethanol was obtained from U.S. Industrial Chemicals Co. Hormones and biochemicals were purchased from Sigma Chemical Co. Animals and Housing. Viral-free immature female Swiss-Webster mice were obtained at 17–19 days of age from Sasco (Omaha, Nebraska) weighing 8–10 g, and were used in the uterotrophic and antiuterotrophic assays. Immature female Sprague-Dawley rats, obtained also at 17–19 days of age from Sasco, weighing 28–33 g, were used in the estradiol receptor binding assay. Animals were housed in wire topped polycarbonate cages with six animals per cage. Environment was controlled at 25° C. with a 12-hour light/dark cycle. The animals received a diet of Wayne Lab Blox rodent chow and tab water ad libitum.

EXAMPLE 7

Uterotrophic Assay

Estrogenic activity of the compounds was determined using a modification of the method of Rubin, B.L., et al., *Endocrinology* 49: 429 (1951) (see Pento, J.T., et al.;1 *J. Endocrinol.* 61: 1216 (1978)) using immature (17–19 days old) female Swiss-Webster mice. The test compounds were dissolved separately in a minimum amount of isopropyl myristate (IPM), and diluted serially with sesame oil to the proper concentrations (final concentration of IPM <5%). Solutions were shaken at 25° C. for several hours to ensure complete dissolution. The mice were randomly separated into groups of six animals, weighed, and the compounds were administered by s.c. injection of 0.1 mL of the oil solutions into the nape of the neck for 3 consecutive days. The solutions were periodically checked by TLC to insure homogeneity. A control group received 0.1 mL sesame oil alone.

The animals were anesthetized with Et$_2$O and sacrificed by cervical dislocation 24h after the last injection. Body weights were determined and the uteri were removed, cleaned of adhering connective tissue and fat, blotted to remove tissue fluid, and weighed to the nearest 0.1 mg.

The compounds shown in Table I, with the exception of compound 11, did not produce any uterotrophic activity in the immature mouse at doses of 30, 150, and 750 μg Compounds 7, 8, 9 and 10 caused a reduction in uterine weight as compared with MER-25 which produced estrogenic responses at the 150 and 750 μg doses.

TABLE I

| (Z)-1,1-Dichloro-2,3-Diarylcyclopropane Derivatives | | |
|---|---|---|
| Compound No. | R | Formula |
| 7 | OSO$_2$CH$_3$ | C$_{18}$H$_{18}$Cl$_2$SO$_4$ |
| 8 | N(CH$_3$)$_2$ | C$_{19}$H$_{21}$Cl$_2$NO |
| 9 | N(CH$_2$CH$_3$)$_2$ | C$_{21}$H$_{25}$Cl$_2$NO |
| 10 | c-NC$_5$H$_{10}$ | C$_{22}$H$_{25}$Cl$_2$NO |
| 11 | c-N(CH$_2$CH$_2$)$_2$N—CH$_3$ | C$_{22}$H$_{26}$Cl$_2$NO |

EXAMPLE 8

Antiuterotrophic Assay

Antiestrogenic activity of the compounds was determined by inhibition of the estradiol-induced uterotrophic activity in immature female Swiss-Webster mice. Animals were distributed into groups of six animals. A modification of the uterotrophic assay described in Example 21 was used (Dorfman, R. I., et al., *Endocrinolooy* 68: 17 (1960)). Estradiol was dissolved in oil (0.1 μg/mL). The test compounds were dissolved in IPM and diluted with IPM to achieve desired concentrations. The solutions were periodically checked by TLC to insure homogeneity. Injections were made in the nape of the neck for 3 consecutive days. The unstimulated control group received vehicles alone (0.05 mL IPM and 0.1 mL sesame oil each day}, while the stimulated control group received 0.1 mL of the estradiol solution (total dose 0.03 μg). All test groups received 0.1 mL of the stimulating dose of estradiol (0.01 μg) plus 0.05 mL of the test compounds solutions each day. The IPM and oil injections were made at separate sites to minimize possible physical or chemical interactions or reduced absorption of either compound. Antiestrogenic activity was measured as a decrease from the estradiol-induced increase in uterine weight seen in the test compound groups versus the estradiol-stimulated group alone.

A series of side-chain derivatives of the antiestrogen, Analog II and MER 25 were examined for estrogen antagonism at doses of 30, 150 and 750 μg against a stimulating does of 0.03 μg of estradiol.

Compounds 8, 9, 10 and 11 produced some antiestrogenic activity, while compound 7 did not (Table II). Compound 9 induced an antiestrogen response of 39.7% as compared to 37.1% of Analog II at 30 and 750 μg dosages respectively. The compounds in Table I did not produce any significant decrease in uterine weight at the highest does of 750 μg but elicited antiestrogenic activity at the lower doses of 30 and 150 μg.

Analog II and MER 25 produced a dose dependent decrease in uterine weight, with MER 25 eliciting the highest observed antiestrogenic activity of 66%. None of the compounds potentiated the uterine weight gain from the stimulating dose of 0.03 μg of estradiol.

TABLE II

Observed Antiestrogenic Activities[a]

| Compound | Total Dose (μg) | % Observed Antiestrogenic Activity[aa] |
|---|---|---|
| 7 | 30 | 7.23 |
|  | 150 | — |
|  | 750 | — |
| 8 | 30 | 9.26 |
|  | 150 | 25.20 |
|  | 750 | 11.25 |
| 9 | 30 | 39.70 |
|  | 150 | 22.44 |
|  | 750 | 15.50 |
| 10 | 30 | 28.41 |
|  | 150 | 33.87 |
|  | 750 | 27.79 |
| 11 | 30 | 10.15 |
|  | 150 | 32.10 |
|  | 750 | 17.53 |
| Analog II | 30 | 24.65 |
|  | 150 | 31.96 |
|  | 750 | 37.12 |
| MER-25 | 30 | 24.46 |
|  | 150 | 24.17 |
|  | 750 | 66.42 |

[a]Determined as the decrease in the estradiol-stimulated (0.03 μg total dose) uterine wt. of immature female mice.
[aa]Calculated by: {(mean uterine wt. of estradiol-stimulated mean − uterine wt. of control) − (mean uterine wt. of test compounds − mean uterine wt. of control)/(mean uterine wt. of estradiol-stimulated − mean uterine wt. of control)} × 100.

EXAMPLE 9

Receptor Binding Assay

The receptor binding activies of the test compounds for the estrogenic receptors were determined by displacement of [$^3$H]-estradiol from rat uterine cytosol in vitro. Female Sprague-Dawley rats (17–19 days old) were treated with 0.53 μg of estradiol in 0.1 mL sesame oil for three consecutive days (total dose 1.6μg). On the fourth day the rats were anesthetized with Et$_2$O and sacrificed by cervical dislocaiton. A modificaiton of Korenman's receptor binding assay method (Korenman, S.G., *Steroids* 13: 163 (1969)) was used. Uteri were removed, cleaned of adhering connective tissue and fat, weighed (avg. wt.=83 mg/animal), and homogenized (Polytron PT-10 stainless steel homogenizer, rheostat setting 7, five ten-second bursts with a ten-second pause between bursts) at 0°–4° C. in five volumes (w/v) of TEDM buffer (10 mM Tris-HCl, 1.5 mM disodium ethylenediamine tetraacetic acid, 1.0 mM dithiothreitol, 10.0 mM sodium molybdate, pH adjusted to 7.4 with 5M NaOH). The resulting homogenate was centrifuged at 2000g for 15 min (4° C.). The supernatant was then centrifuged at 104,000g for 1 h (4° C.). The supernatant from the high speed centrifugation (cytosol) was carefully decanted and used immediately. The protein content of the cytosol was determined and adjusted to 4–5 mg protein/mL. The test compounds were dissolved in EtOH or DMSO and diluted with TEDM so that the final EtOH concentration was less than 2% or the final DMSO concentration was less than 10%. Neither of these concentrations of the organic solvents affected the binding of the tritiated estradiol to the cytosolic receptor or the amount of non-specific binding seen as determined by parallel incubations. Duplicate incubations were conducted at 4° C. for 24 h in a total volume of 0.5 mL containing: 200 μL cytosol; 100 μL (0.218 μCi) of 2,4,6, 7(n)-[$^3$H]-17β-estradiol (93.35 mCi/mmole); 100 μL of the test compounds at concentrations ranging from $10^{-4}$ to $10^{-6}$ M, or unlabelled estradiol at concentrations ranging from $10^{-6}$ to $10^{-8}$ M; and sufficient TEDM to obtain a final volume of 0.5 mL. Single parallel incubations at each concentration of test compound and estradiol contained 100 μL of $2\times10^{-5}$ M DES in the final TEDM addition to distinguish between specific receptor binding and non-specific protein/receptor binding of the compounds.

After incubation, 0.5 mL of a Dextran-Coated Charcoal (DCC) solution (0.5% activated charcoal and 0.05% Dextran T-70, w/v, in TEDM buffer) was added and the tubes were gently vortexed at 4° C. 15 min. The tubes were centrifuged at 2000g 15 min (4° C.) to remove the unbound [$^3$H]-estradiol. A 0.5 mL aliquot of the supernatant was added to 10 mL Beckmann Ready-Solv VI scintillation cocktail in subdued light and the tritium content of each vial was determined by liquid scintillation spectrometry. The radioactivity was plotted as a function of the log concentration of competing ligand and subjected to linear regression analysis. Relative binding affinity of each compound was determined by the method of Bliss, C.I., *The Statistics of Bioassay*, *Academic Press* (New York 1952).

The compounds in Table I produced no displacement of [$^3$H]-estradiol from the rat uterine cytosol, while tamoxifen and Analog II produced a parallel displacement with estradiol indicating a relative binding affinity for the ER. Both the free bases and the citrate salts of the compounds were tested in the ER binding assay.

EXAMPLE 10

Statistical Analysis

The relative binding affinity determinations were performed by a TI-59 programmable calculator (Texas Instruments). The Student's t-test (non-paired) was used to compare individual treatment groups to the estradiol group statistically. Multiple group comparison were analyzed by ANOVA. P or F values of less than 0.05 were considered to be significant. The Student's t values, ANOVA F values, linear regression and standard errors were obtained by Cricket Graph and StatWorks programs on a MacIntosh computer.

EXAMPLE 11

The compounds shown in Table I were found to be devoid of estrogenic activity, but possessed a small degree of antiestrogenic activity in the mouse. These compounds produced a 10 to 37% decrease in estradiol-stimulated uterotropic activity at the doses tested (see Table II). None of the cyclopropyl side-chain compounds (Table I) displaced [$^3$H]-estradiol from the ER in the rat uterine cytosol as determined by the competitive binding assay. Since it is known that there is a correlation between ER binding affinity and estrogenic activity, it can be assumed from the receptor binding data that the compounds, which were poor binders, lacked estrogenic activity. As observed in the uterotrophic assay, none of the compounds (Table I) increased uterine weight as compared to the non-treated control group and they did not potentiate the uterotrophic response of the stimulating dose of estradiol in the antiuterotrophic assay, clearly indicating that the compounds are not estrogenic in the mouse. Analog II and MER-25 used as standards, elicited a significant decrease in uterine weight only at the highest tested dose of 750 μg. The structure of Analog II is as follows:

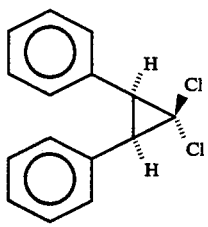

EXAMPLE 12

In Vitro testing of MCF-7, Human Breast Cell Cancer Line

MCF-7 Cell Culture Method. MCF-7 human breast cancer cells were obtained from the Michigan Cancer Foundation. MCF-7 cells were grown at 37° C. in 75 cm$^2$ tissue culture (T-75) flasks, as monolayer cultures in RPMI 1640 media (without phenol red) supplemented with 2 mM 1-glutamine, gentamicin (50 μg/mL), penicillin (100 units/mL), streptomycin (100 μg/mL) and calf serum (5%). Cultures were grown in an incubator at 37° C. in a humid 5% CO$_2$ atmosphere, and fed on alternate days. Exponential growth was maintained by subculturing at eight day intervals when the cell number per T-75 flask reached 10 to 25×10$^6$ cells.

All of the compounds were tested for their ability to alter the growth of MCF-7 cells at a concentration ranging from $10^{-4}$ to $10^{-6}$ M. Growth inhibition produced at concentrations greater than $5\times10^{-6}$ M are considered to be cytotoxic anti-tumor effects. Control samples received vehicle alone at the same concentrations used in the treatment groups.

In each experiment, the cells were trypsinized, washed and plated in multiwell plates at a density of $5\times10^4$ cells/well in 3 mL of RPMI 1640 media. Cells were allowed to attach and were in logarithmic growth when the test compounds were added. Each group was done in triplicate. The test compounds were dissolved in a polyethylene glycol 400:ethanol (55:45) mixture and added in the culture media. The final concentration of the vehicle mixture was 0.1% of the incubation media. Cell growth was measured on alternate days using the hemocytometric trypan blue exclusion method.

Statistics. The student's t-test (non-paired) was used to make statistical comparisons between two experimental groups. Multiple group comparisons in the cell culture experiments were made using a 3-way ANOVA. P values of less than 0.05 were considered to be statistically significant. The student's t values, standard errors, and linear regression were obtained using the Stat Work and Cricket Graph programs on a Macintosh computer.

Results. The results of the MCF-7 human breast cancer cell culture study indicate that compound 10 abolished cell growth at $10^{-4}$ M (Table III), significantly reduced cell growth at $10^{-5}$ M (Table IV), and had no effect on cell growth at $10^{-6}$ M (Table V). These data indicate that compound 10 is cytotoxic to human breast cancer cells in culture. Cell growth was inhibited by tamoxifen (a known antiestrogen) at a concentration of $10^{-6}$ M confirming the estrogen-specific nature of the MCF-7 cell used in this study.

TABLE III

Effect of $10^{-4}$M Compound 10 on Cell Growth

| Days | Control | Mean Live Cell Count Per Well Compound 10, $10^{-4}$M | Tamoxifen, $10^{-6}$M |
|---|---|---|---|
| 0 | 81,481 | 81,481 | — |
| 2 | 158,333 | — | — |
| 4 | 256,944 | 5,324 | — |
| 6 | 235,417 | 1,620 | — |

TABLE IV

Effect of $10^{-5}$M Compound 10 on Cell Growth

| Days | Control | Mean Live Cell Count Per Well Compound 10, $10^{-5}$M | Tamoxifen, $10^{-6}$M |
|---|---|---|---|
| 0 | 118,056 | 118,056 | 118,056 |
| 2 | 227,315 | 115,741 | 248,611 |
| 4 | 474,074 | 186,111 | 332,407 |
| 6 | 648,148 | 50,000 | 547,222 |

TABLE V

Effect of $10^{-6}$M Compound 10 on Cell Growth

| Days | Control | Mean Live Cell Count Per Well Compound 10, $10^{-6}$M | Tamoxifen, $10^{-6}$M |
|---|---|---|---|
| 0 | 91,204 | 91,204 | 91,204 |
| 2 | 149,537 | 215,278 | 105,093 |
| 4 | 415,741 | 430,556 | 387,963 |
| 6 | 526,389 | 537,037 | 647,222 |

All U.S. patent applications and publications cited herein are hereby incorporated by reference.

Changes may be made in the embodiments of the invention described herein or in parts or elements of the embodiments described herein or in the steps or in the sequence of steps of the methods described herein without departing from the spirit and scope of the invention as defined in the following claims.

What is claimed is:

1. A compound having the formula:

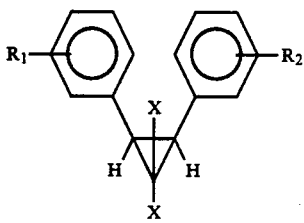

or any pharmaceutically acceptable salt thereof, in which:
X is selected from a group consisting of,
halogen atoms and
hydrogen atoms;
$R_1$ is selected from a group consisting of,
a hydrogen atom, and
a substituted alkoxy group in which the substituent of the alkoxy group is selected from a group consisting of,
an unsubstituted piperidino, and
a substituted piperidino in which the substitutent is an alkyl group containing from 1 to 6 carbon atoms; and
$R_2$ is selected from a group consisting of
a hydrogen atom, and
a substituted alkoxy group, and in which the substituent of the alkoxy group is selected from a group consisting of,
an unsubstituted piperidino, and
a substituted piperidino in which the substituent is an alkyl group containing from 1 to 6 carbon atoms; and
with the proviso that $R_1$ and $R_2$ cannot be simultaneously hydrogen.

2. The compound of claim 1 in which $R_1$ is selected from a group consisting of;
a substituted alkoxy in which the substituent is a piperidino; and
a substituted alkoxy in which the substituent is a substituted piperidino and in which the piperidino substituent is an alkyl group.

3. The compound of claim 2 in which $R_2$ is hydrogen.

4. The compound of claim 3 in which $R_1$ and the $R_2$ are each at the para ring position.

5. The compound of claim 4 in which X is chlorine.

6. The compound of claim 1 in which $R_2$ is selected from a group consisting of:
a substituted alkoxy group in which the substituent is a piperidino and
a substituted alkoxy in which the substituent is a substituted piperidino and in which the piperidino substituent is an alkyl group.

7. The compound of claim 6 in which $R_1$ is hydrogen.

8. The compound of claim 7 in which the $R_1$ and the $R_2$ are each at the para ring position.

9. The compound of claim 8 in which X is chlorine.

10. A composition of matter comprising:
a pharmaceutically acceptable carrier; and
a compound having the formula:

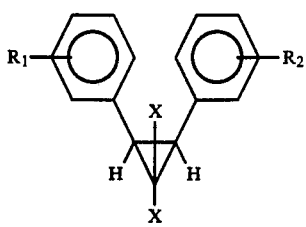

or any pharmaceutically acceptable salt thereof and a pharmaceutically acceptable carrier of sufficient quantity to solubilize the compound, in which:
X is selected from a group consisting of,
halogen atoms and
hydrogen atoms;
$R_1$ is selected from a group consisting of,
a hydrogen atom,
a hydroxyl group, and
a substituted alkoxy group in which the substituent of the alkoxy group is selected from a group consisting of,
an unsubstituted piperidino, and
a substituted piperidino in which the substituent is an alkyl group containing from 1 to 6 carbon atoms; and
$R_2$ is selected from a group consisting of,
a hydrogen atom, and
a substituted alkoxy group, and in which the substituent of the alkoxy group is selected from a group consisting of,
an unsubstituted piperidino, and
a substituted piperidino in which the substituent is an alkyl group containing from 1 to 6 carbon atoms; and
with the proviso that $R_1$ and $R_2$ cannot be simultaneously hydrogen.

11. The compound of claim 10 in which $R_1$ is selected from a group containing:
a substituted alkoxy in which the substituent is a piperidino; and
a substituted alkoxy in which the substituent is a substituted piperidino and in which the piperidino substituent is an alkyl group.

12. The compound of claim 11 in which R2 is hydrogen.

13. The compound of claim 12 in which the $R_1$ and the R2 are each at the para ring position.

14. The compound of claim 13 in which X is chlorine.

15. The compound of claim 10 in which $R_2$ is selected from a group consisting of:
a substituted alkoxy in which the substituent is a piperidino and
a substituted alkoxy in which the substituent is a substituted piperidino and in which the piperidino substitutent is an alkyl group.

16. The compound of claim 15 in which R1 is hydrogen.

17. The compound of claim 16 in which the $R_1$ and the $R_2$ are each at the para ring position.

18. The compound of claim 17 in which X is chlorine.

19. A method of inducing antiestrogenic activity in a mammal in need of each therapy comprising administering to the mammal an antiestrogenically effective amount of one or more compounds having the formula:

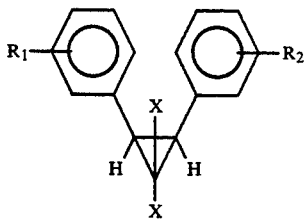

or any pharmaceutically acceptable salt thereof, in which:
X is selected from a group consisting of,
  halogen atoms and
  hydrogen atoms;
$R_1$ is selected from a group consisting of,
  a hydrogen atom, and
  a substituted alkoxy group in which the substituent of the alkoxy group is selected from a group consisting of,
    an unsubstituted piperidino, and
    a substituted piperidino in which the substituent is an alkyl group containing from 1 to 6 carbon atoms; and
$R_2$ is selected from a group consisting of,
  a hydrogen atom,
  a substituted alkoxy group in which the substituent of the alkoxy group is selected from a group consisting of
    an unsubstituted piperidino, and
    a substituted piperidino in which the substituent is an alkyl group containing from 1 to about 6 carbon atoms, and
with the proviso that $R_1$ and $R_2$ cannot be simultaneously hydrogen.

20. The method of claim 19 in which $R_1$ is selected from a group consisting of:
  a substituted alkoxy in which the substituent is a piperidino, and
  A substituted alkoxy in which the substituent is a substituted piperidino and in which the piperidino substituent is an alkyl group.

21. The method of claim 20 in which $R_2$ is hydrogen.

22. The method of claim 21 in which the $R_1$ and the $R_2$ are each at the para ring position.

23. The method of claim 22 in which X is chlorine.

24. The method of claim 19 in which $R_2$ is selected from a group consisting of:
  a substituted alkoxy in which the substituent is a piperidino and
  a substituted alkoxy in which the substituent is a substituted piperidino and in which the piperidino substituent is an alkyl group.

25. The compound of claim 24 in which $R_1$ is hydrogen.

26. The compound of claim 25 in which $R_1$ and $R_2$ are each at the para ring position.

27. The compound of claim 26 in which X is chlorine.

28. A method of inhibiting the development of an estrogen-dependent tumor in a mammal in need of such therapy comprising administering to the mammal an effective amount of one or more compounds having the formula:

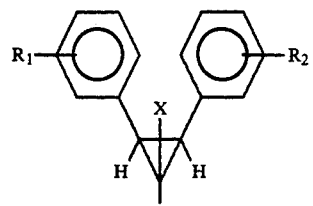

or any pharmaceutically acceptable salt thereof, in which:
X is selected from a group consisting of,
  halogen atoms and
  hydrogen atoms;
$R_1$ is selected from a group consisting of,
  a hydrogen atom,
  a substituted alkoxy group in which the substituent of the alkoxy group is selected from a group consisting of
  and
    an unsubstituted piperidino and
    a substituted piperidino in which the substituent is an alkyl group containing from 1 to 6 carbon atoms;
$R_2$ is selected from a group consisting of,
  a hydrogen atom, and
  a substituted alkoxy group in which the substituent of the alkoxy group is selected from the group consisting of,
    an unsubstituted piperidino and
    a substituted piperidino in which the substituent is an alkyl group containing from 1 to 6 carbon atoms; and
with the proviso that $R_1$ and $R_2$ cannot be simultaneously hydrogen.

29. The method of claim 28 in which $R_1$ is selected from a group consisting of:
  a substituted alkoxy in which the substituent is a piperidino and
  a substituted alkoxy in which the substituent is a substituted piperidino and in which the piperidino substituent is an alkoxy group.

30. The method of claim 29 in which R2 is hydrogen.

31. The method of claim 30 in which $R_1$ and $R_2$ are each at the para ring position.

32. The method of claim 31 in which X is chlorine.

33. The method of claim 28 in which $R_2$ is selected from a group consisting of:
  a substituted alkoxy in which the substituent is a piperidino.

34. The compound of claim 33 in which R1 is hydrogen.

35. The compound of claim 34 in which $R_1$ and $R_2$ are each at the para ring position.

36. The compound of claim 35 in which X is chlorine.

37. The compound of claim 1 in which X is chlorine, $R_1$ is a piperidinoethoxy group, and $R_2$ is hydrogen.

38. The compound of claim 1 in which X is chlorine, $R_1$ is hydrogen and $R_2$ is a piperidinoethoxy group.

39. The compound of claim 10 in which X is chlorine, $R_1$ is a piperidinoethoxy group, and $R_2$ is hydrogen.

40. The compound of claim 10 in which X is chlorine, $R_1$ is hydrogen and $R_2$ is a piperidinoethoxy group.

41. The compound of claim 19 in which X is chlorine, $R_1$ is a piperidinoethoxy group, and $R_2$ is hydrogen.

42. The compound of claim 19 in which X is chlorine, $R_1$ is hydrogen and $R_2$ is a piperidinoethoxy group.

43. The compound of claim 28 in which X is chlorine, $R_1$ is a piperidinoethoxy group, and $R_2$ is hydrogen.

44. The compound of claim 28 in which X is chlorine, $R_1$ is hydrogen and $R_2$ is a piperidinoethoxy group.

* * * * *

UNITED STATES PATENT AND TRADEMARK OFFICE
CERTIFICATE OF CORRECTION

PATENT NO. : 5,324,736         Page 1 of 3
DATED      : June 28, 1994
INVENTOR(S): Magarian et al.

It is certified that error appears in the above-indentified patent and that said Letters Patent is hereby corrected as shown below:

Column 2, line 60, please delete "Perferably", and substitute therefore --Preferably--.

Column 2, line 62, please delete "perferably", and substitute therefore --preferably--.

Column 3, line 44, after "mixtures", please insert --thereof of optical isomers having the same chemical structures are within the scope of the present invention.--.

Column 6, line 41, please delete "Kuqelrohr", and substitute therefore --Kugelrohr--.

Column 7, line 11, please delete "extracte" and substitute therefore --extracted--.

Column 7, line 60, please delete "330", and substitute therefore --3.30--.

Column 8, line 42, after "equal", please insert --molar--.

Column 8, line 43, after "EtOH", please insert --.--.

UNITED STATES PATENT AND TRADEMARK OFFICE
CERTIFICATE OF CORRECTION

PATENT NO. : 5,324,736
DATED : June 28, 1994
INVENTOR(S) : Magarian et al.

It is certified that error appears in the above-indentified patent and that said Letters Patent is hereby corrected as shown below:

Column 8, lines 43-44, after "Etoh", please delete "and treated with an equal molar amount of citric acid in hot EtOH."

Column 9, line 15, please delete "phenylcyclopropanc", and substitute therefore --phenylcyclopropane--.

Column 9, line 23, before "t", please insert --(--.

Column 11, line 24, please delete "does", and substitute therefore --dose--.

Column 11, line 32, please delete "does", and substitute therefore --dose--.

Column 13, line 68, please delete "25", and substitute therefore --12--.

UNITED STATES PATENT AND TRADEMARK OFFICE
CERTIFICATE OF CORRECTION

PATENT NO. : 5,324,736
DATED : June 28, 1994
INVENTOR(S) : Magarian et al.

It is certified that error appears in the above-indentified patent and that said Letters Patent is hereby corrected as shown below:

Column 16, line 67, please delete "each", and substitute therefore --such--.

Column 18, line 48, after "peridino", please insert --and a substituted alkoxy in which the substituent is a substituted piperidino and in which the piperidino substituent is an alkyl group--.

Signed and Sealed this

Tenth Day of January, 1995

Attest:

BRUCE LEHMAN

Attesting Officer

Commissioner of Patents and Trademarks